US008983234B2

(12) United States Patent
Holt

(10) Patent No.: US 8,983,234 B2
(45) Date of Patent: Mar. 17, 2015

(54) METHOD AND APPARATUS PERTAINING TO USING IMAGING INFORMATION TO IDENTIFY A SPECTRUM

(71) Applicant: Varian Medical Systems, Inc., Palo Alto, CA (US)

(72) Inventor: Kevin M. Holt, Chicago, IL (US)

(73) Assignee: Varian Medical Systems, Inc., Palo Alto, CA (US)

( * ) Notice: Subject to any disclaimer, the term of this patent is extended or adjusted under 35 U.S.C. 154(b) by 117 days.

(21) Appl. No.: 13/630,269

(22) Filed: Sep. 28, 2012

(65) Prior Publication Data

US 2014/0090491 A1 Apr. 3, 2014

(51) Int. Cl.

| | |
|---|---|
| ***G06K 9/32*** | (2006.01) |
| ***A61B 8/08*** | (2006.01) |
| ***G01J 3/28*** | (2006.01) |
| ***G01N 23/04*** | (2006.01) |
| *A61B 6/00* | (2006.01) |

(52) U.S. Cl.

CPC ............... *A61B 6/482* (2013.01); *A61B 6/4241* (2013.01); *A61B 6/5217* (2013.01); *A61B 6/583* (2013.01); *A61B 8/08* (2013.01); *G01J 3/28* (2013.01); *G01N 23/04* (2013.01); *G01N 2223/401* (2013.01); *G01N 2223/423* (2013.01)

USPC .......................................................... 382/294

(58) Field of Classification Search

CPC ......... G06T 5/50; G06T 11/00; G06T 11/003; G06T 11/006; G06T 11/008; G06T 2207/10081; G06T 2207/10088; G06T 2207/10116; G06K 9/00201; H04N 2201/00; H04N 2201/0079; G01T 3/00; G01V 5/0041; G01V 5/0091

See application file for complete search history.

(56) References Cited

U.S. PATENT DOCUMENTS

| | | | |
|---|---|---|---|
| 4,511,799 | A | 4/1985 | Bjorkholm |
| 5,319,547 | A | 6/1994 | Krug et al. |
| 5,479,255 | A | 12/1995 | Denny et al. |
| 5,481,584 | A | 1/1996 | Tang et al. |
| 5,524,133 | A | 6/1996 | Neale et al. |
| 5,548,123 | A | 8/1996 | Perez-Mendez et al. |
| 5,917,880 | A | 6/1999 | Bjorkholm |

(Continued)

OTHER PUBLICATIONS

Ahn, Jae Yul; Authorized Officer; PCT Search Report and Written Opinion from related PCT/US2013/061302 dated Dec. 19, 2013; 13 pages.

(Continued)

*Primary Examiner* — Jose Couso

(74) *Attorney, Agent, or Firm* — Fitch, Even, Tabin & Flannery LLP

(57) ABSTRACT

A control circuit operably couples to a non-invasive imaging system that utilizes a particular corresponding effective spectrum and receives imaging information as pertains to an object being imaged. The control circuit uses that information to identify the particular corresponding spectrum for the corresponding source of radiation by, at least in part, evaluating candidate spectra as a function, at least in part, of physical likelihood (for example, by identifying a spectrum that is physically unlikely or physically impossible). Evaluating the candidate spectra as a function of physical likelihood can comprise evaluating the candidate spectra with respect to regularization, smoothness, being non-negative, normalization characteristics, monotonic characteristics, envelope limitations, quasi-concave characteristics, and/or consistency with one or more physics models of choice to note but a few options in these regards.

20 Claims, 2 Drawing Sheets

AT A CONTROL CIRCUIT OPERABLY COUPLED TO A NON-INVASIVE IMAGING APPARATUS THAT UTILIZES A PARTICULAR CORRESPONDING SPECTRUM

101 RECEIVING IMAGING INFORMATION AS PERTAINS TO AN OBJECT BEING IMAGED BY THE NON-INVASIVE IMAGING APPARATUS

102 USING THE IMAGING INFORMATION TO IDENTIFY THE PARTICULAR CORRESPONDING SPECTRUM FOR THE SOURCE OF RADIATION BY, AT LEAST IN PART, EVALUATING CANDIDATE SPECTRA AS A FUNCTION, AT LEAST IN PART, OF PHYSICAL LIKELIHOOD

103 SELECT A PARTICULAR SPECTRUM AS A FUNCTION, AT LEAST IN PART, OF THE EVALUATING OF THE CANDIDATE SPECTRA TO THEREBY PROVIDE AT LEAST ONE SELECTED SPECTRUM

104 USE THE AT LEAST ONE SELECTED SPECTRUM WHEN LATER USING OTHER IMAGING INFORMATION FROM THE NON-INVASIVE IMAGING APPARATUS TO DETERMINE A MATERIAL CONSTITUENCY OF ANOTHER OBJECT OF UNCERTAIN MATERIAL CONSTITUENCY

100

(56) References Cited

U.S. PATENT DOCUMENTS

| | | | | |
|---|---|---|---|---|
| 6,069,936 | A | 5/2000 | Bjorkholm | |
| 6,597,759 | B2 * | 7/2003 | Mazess et al. | 378/53 |
| 7,132,652 | B1 | 11/2006 | Testoni | |
| 7,257,188 | B2 * | 8/2007 | Bjorkholm | 378/53 |
| 7,636,417 | B2 | 12/2009 | Bjorkholm | |
| 7,876,874 | B2 | 1/2011 | Goto et al. | |
| 7,945,017 | B2 * | 5/2011 | Chen et al. | 378/57 |
| 8,290,230 | B2 * | 10/2012 | Chen et al. | 382/131 |
| 2007/0183568 | A1 | 8/2007 | Kang et al. | |
| 2008/0037707 | A1 | 2/2008 | Rothschild et al. | |
| 2009/0129544 | A1 | 5/2009 | Chen et al. | |
| 2011/0129066 | A1 | 6/2011 | Statham et al. | |

OTHER PUBLICATIONS

Alvarez, Robert E. et al., "Energy-Selective Reconstructions in X-ray Computerized Tomography," Phys. Med. Biol., vol. 21, No. 5, pp. 733-744; 1976.

Baird, L. C.; "X-ray Spectra vs Attenuation Data: A Theoretical Analysis;" Medical Physics, vol. 8, No. 3, May/Jun. 1981; pp. 319-323.

Archer, Benjaimin R. et al.; "A Laplace Transform Pair Model for Spectral Reconstruction;" Medical Physics, vol. 9, No. 6, Nov./Dec. 1982; pp. 844-847.

Archer, Benjamin R. et al.; "Application of a Laplace Transform Pair Model for High-Energy X-Ray Spectral Reconstruction;" Medical Physics, vol. 12, No. 5, Sep./Oct. 1985; pp. 630-633.

Archer, Benjamin R. et al.; "Analysis of Errors in Spectral Reconstruction with a Laplace Transform Pair Model;" Phys. Med. Biol., vol. 30, No. 5, 1985; pp. 411-418.

Archer, Benjamin R. et al.; "Laplace Reconstruction of Experimental Diagnostic X-Ray Spectra;" Medical Physics, vol. 15, No. 6, Nov./Dec. 1988; pp. 832-837.

Maitrejean et al., "Multi-Energy Method: A New Approach for Measuring X-Ray Transmission as Function of Energy with a Bremsstrahlung Source. Application for Heavy Element Identification," Proceedings for the International Society for Optical Engineering; vol. 3446; Jul. 22, 1988; pp. 114-133.

Ogorodnikov et al., "Processing of Interlaced Images in 4-10 MeV Dual Energy Customs System for Material Recognition," Physical Review Special Topics-Accelerators and Beams, vol. 5, 104701 (2002); 11 pages.

Srebro, Nathan et al., "Weighted Low-Rank Approximations," Proceedings of the Twentieth International Conference on Machine Learning (ICML-2003), Washington DC; 2003; 8 pages.

Rebuffel et al., "Dual-Energy X-Ray Imaging: Benefits and Limits," Insight (Non-Destructive Testing and Condition Monitoring, British Institute of Non-Destructive Testing; vol. 40, Issue 10; Oct. 1, 2007; pp. 589-594.

Xu, Dan et al.; "Dual Energy CT Via Fast kVp Switching Spectrum Estimation;" Medical Imaging 2009: Physics of Medical Imaging; SPIE vol. 7258; 2009; 10 pages.

Extended European Search Report from related European Patent Application No. 10164833.5; Oct. 19, 2010; 5 pages.

Extended European Search Report from related European Patent Application No. 10164828.5; Oct. 26, 2010; 7 pages.

Holt, Kevin M., "Angular Regularization of Vector-Valued Signals," 2011 IEEE International Conference on Acoustics, Speech and Signal Processing (ICASSP); Prague, Czech Republic; May 2011; 4 pages.

* cited by examiner

METHOD AND APPARATUS PERTAINING TO USING IMAGING INFORMATION TO IDENTIFY A SPECTRUM

RELATED APPLICATION(S)

This application is related to co-pending and co-owned U.S. patent application Ser. No. 12/479,322, entitled Method and Apparatus to Facilitate Using Fused Images to Identify Materials and filed Jun. 5, 2009, which is incorporated by reference in its entirety herein.

This application is also related to co-pending and co-owned U.S. patent application Ser. No. 13/277,833, entitled Method and Apparatus Pertaining to Non-Invasive Identification of Materials and filed Oct. 20, 2011, which is incorporated by reference in its entirety herein.

TECHNICAL FIELD

This invention relates generally to non-invasive approaches to imaging and the spectrum utilized to obtain the images.

BACKGROUND

Various non-invasive approaches to imaging are known in the art. This can include, for example, the use of x-rays to form one or more images of a given object. Such images can serve a variety of purposes. As but one example in these regards, a number of images of a same object formed using a corresponding variety of x-ray source energies and/or detector spectral responses can facilitate identifying the material (or materials) that comprises that object.

Properly interpreting such images typically presumes a considerable amount of information regarding the imaging spectrum itself. Manufacturers of non-invasive imaging apparatuses often provide general (or even machine-specific) specifications for their machines. For example, information regarding the spectrum utilized by a given apparatus may be characterized as a given number of half-value layers (HVL's). Such information can be useful for many purposes.

Unfortunately, however, such information may be insufficient to accommodate the needs of all application settings. For example, the information may only represent an average or median representation of a family of machines offered by a given manufacturer. As another example such information may be too coarse to support some desired uses.

There have been some attempts in the prior art to estimate the spectral response of a given imaging system. These prior art approaches have utilized, for example, Laplace transform methods, Monte Carlo-based approaches, and even a basis-sum approach. Unfortunately, such approaches are not adequate to address the needs of all application settings.

BRIEF DESCRIPTION OF THE DRAWINGS

The above needs are at least partially met through provision of the method and apparatus pertaining to using imaging information to identify spectrum described in the following detailed description, particularly when studied in conjunction with the drawings, wherein.

Figure 1:
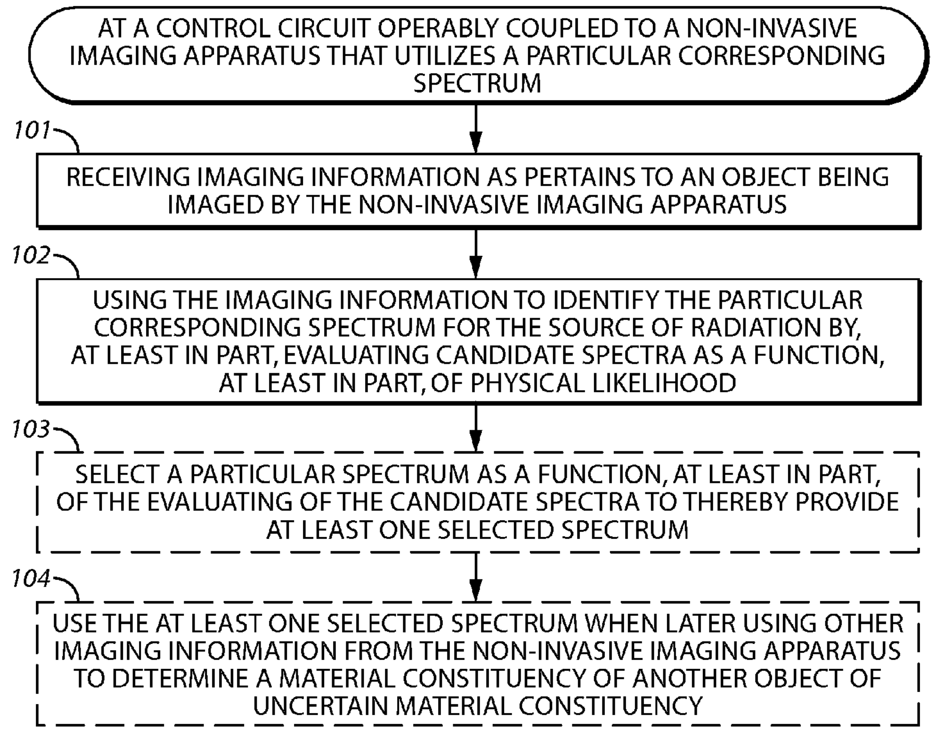
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit that operably couples to a non-invasive imaging system that utilizes a particular corresponding effective spectrum receives imaging information as pertains to an object being imaged by that non-invasive imaging apparatus. The control circuit then uses that imaging information to identify the particular corresponding spectrum for the corresponding source of radiation by, at least in part, evaluating candidate spectra as a function, at least in part, of physical likelihood (for example, by identifying a spectrum that is physically unlikely or physically impossible).

The present teachings will accommodate a variety of practices in these regards. By one approach, for example, evaluating the candidate spectra as a function of physical likelihood can comprise evaluating the candidate spectra with respect to regularization, smoothness, being non-negative, normalization characteristics, monotonic characteristics, envelope limitations, quasi-concave characteristics, and/or consistency with one or more physics models of choice.

The present teachings are highly flexible in practice. As one example in these regards, the aforementioned imaging information can pertain to a plurality of objects that are being simultaneously imaged by the non-invasive imaging apparatus.

So configured, such an approach can serve to facilitate then selecting a particular spectrum as a function, at least in part, of having evaluated the candidate spectra to thereby provide at least one selected spectrum. The control circuit can then use that selected spectrum when later using other imaging information from the non-invasive imaging apparatus to determine a material constituency of another object of uncertain material constituency.

These teachings can serve to characterize the spectrum of a given imaging apparatus to a degree of precision that exceeds the norm. Knowing the spectrum in more precise terms, in turn, can better inform any of a variety of analyses and calculations that serve to leverage the imaging information gleaned by use of the characterized spectrum.

These and other benefits may become clearer upon making a thorough review and study of the following detailed description. Referring now to the drawings, and in particular to FIG. 1, an illustrative process 100 that is compatible with many of these teachings will now be presented.

Figure 2:
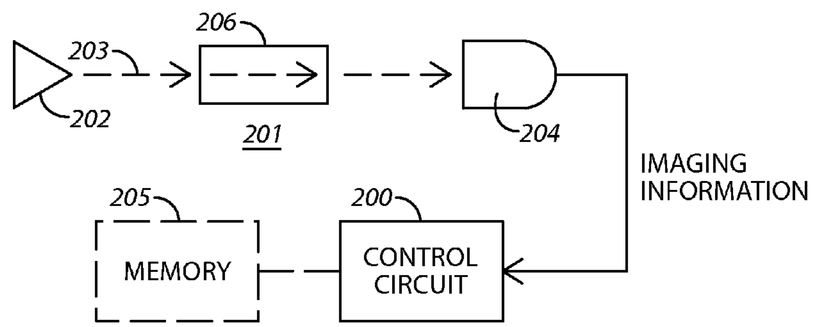
FIG. 2 comprises a block diagram as configured in accordance with various embodiments of the invention.

For the sake of an illustrative example, it will be presumed for the purposes of this description that a control circuit of choice carries out this process 100. With momentary reference to FIG. 2, this control circuit 200 can operably couple to a non-invasive imaging apparatus 201 that utilizes a particular corresponding spectrum 203 as emitted by one or more radiation sources 202 of choice (such as, for example, an x-ray radiation source). This non-invasive imaging apparatus 201 can further include one or more detectors 204 that provides corresponding detection results (i.e., imaging information) to the control circuit 200. The detector may itself have one or more spectral response(s), which also affect(s) the effective spectrum.

Such a control circuit 200 can comprise a fixed-purpose hard-wired platform or can comprise a partially or wholly programmable platform. All of these architectural options are well known and understood in the art and require no further description here. This control circuit 201 is configured (for example, by using corresponding programming as will be well understood by those skilled in the art) to carry out one or more of the steps, actions, and/or functions described herein.

By one optional approach a memory 205 can also operably couple to the control circuit 200. This memory 205 may be integral to the control circuit 200 or can be physically discrete (in whole or in part) from the control circuit 200 as desired. This memory 205 can also be local with respect to the control circuit 200 (where, for example, both share a common circuit board, chassis, power supply, and/or housing) or can be partially or wholly remote with respect to the control circuit 200 (where, for example, the memory 205 is physically located in another facility, metropolitan area, or even country as compared to the control circuit 200).

This memory 205 can serve, for example, to non-transitorily store the computer instructions that, when executed by the control circuit 200, cause the control circuit 200 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

Figure 3:
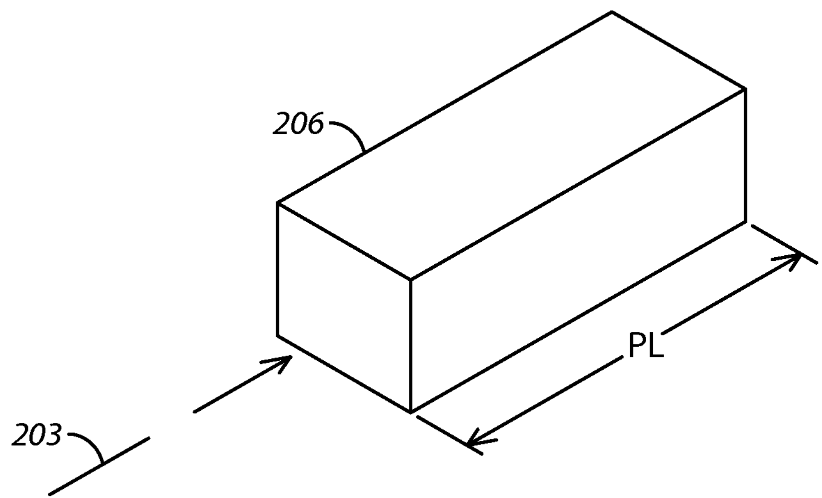
FIG. 3 comprises a perspective view as configured in accordance with various embodiments of the invention.

So configured, the aforementioned detector 204 gathers data regarding how one or more objects 206 interact with the radiated energy from the radiation source 202 and provides this information (as raw and unprocessed or as pre-processed (for example, by correcting for electronic offsets and/or so-called dark current, air normalization, and/or source fluctuations) as may be desired) to the control circuit 200. Generally speaking, non-invasive imaging apparatuses are well known in the art and comprise a well-understood area of endeavor. As the present teachings are not overly sensitive to any particular choices in these regards, further elaboration regarding such an apparatus will not be provided here for the sake of brevity and clarity. Referring again to FIG. 1, at step 101 this process 100 provides for receiving imaging information as pertains to an object 206 being imaged by the non-invasive imaging apparatus 201. These teachings are highly flexible in these regards and will accommodate a wide variety of object shapes and types. Generally speaking, the object 206 has physical properties (such as, for example, one or more of shape, path-length dimension, density (represented, for example, as grams per cubic centimeter), and material composition) that are known a priori. (As illustrated in FIG. 3, path-length dimension PL refers to a dimension (typically measured in a linear unit such as millimeters or centimeters) of the object 206 that is coaxial with and parallel to the emitted radiation 203 from the radiation source 202.)

For example, it can be known prior to conducting this process 100 that the object 206 is made of essentially pure lead and has a uniform path-length dimension of 10 centimeters. As another example in these regards it may be sufficient to know the projected density (usually in grams per cubic centimeter) and the composition (as an expressed percentage, for example, of each element) where composition is expressed as percentages of the total mass of the object.

Figure 4:
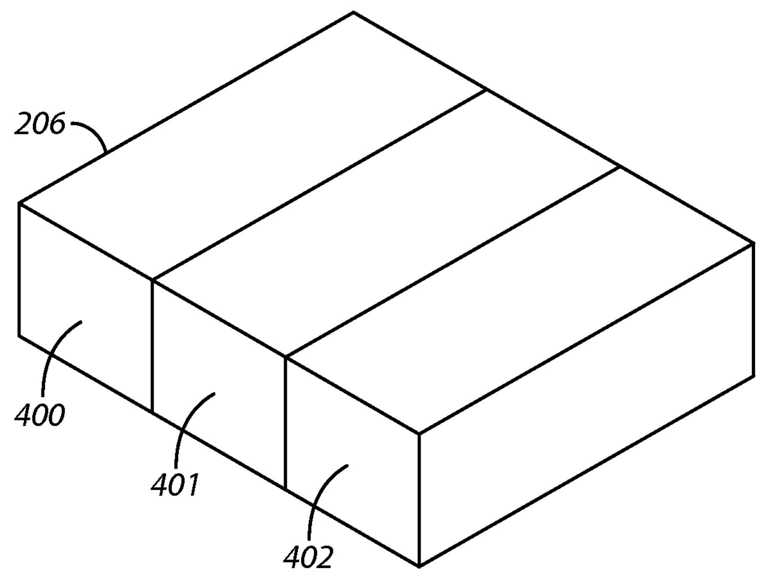
FIG. 4 comprises a perspective view as configured in accordance with various embodiments of the invention.

The object 206 can comprise an object that comprises only a single element or can comprise a multi-element object. As shown in FIG. 4, for example, a given object 206 can be comprised of a variety of sections 400-402 that are each comprised of a different material. As another example, the object 206 can comprise a single common material but shaped so as to have a plurality of different path-length dimensions. As another example, the object 206 can comprise a number of different materials, each in a plurality of different path-length dimensions. These teachings will also accommodate receiving imagining information as pertains to a plurality of discrete objects 206 that are being simultaneously imaged by the non-invasive imaging apparatus 201.

Referring again to FIG. 1, at step 102 the control circuit 200 then uses that imaging information to identify the particular corresponding effective spectrum representing the spectrum for the source of radiation 202 and/or the spectral response of the detector 204. Pursuant to this process 100 the control circuit 200 achieves this result, at least in part, by evaluating candidate spectra as a function of physical likelihood. This evaluation can comprise, for example identifying at least one candidate spectrum that is physically unlikely or even physically impossible. Physically unlikely or impossible candidate spectrums can then be eliminated (at least temporarily) from consideration as the actual spectrum for the source of radiation 202.

These teachings will accommodate a variety of ways by which the candidate spectra can be evaluated for physical likelihood. By one approach, and generally speaking, the control circuit 200 can evaluate some or all of the candidate spectra with respect to regularization. Generally speaking, regularization is a known approach that often involves introducing additional criteria in order to solve an ill-posed problem or to prevent overfitting. This additional information often assumes the form of a penalty for complexity, such as a penalty on bumpiness (which encourages a smooth answer), or more generally, a penalty on how much information it takes to represent an answer (which encourages the answer to lie in or close to some restricted space).

To be more specific, here are a number of criteria by which the control circuit 200 can evaluate the physical likelihood of a given candidate spectra pursuant to this step 102:

Smoothness—Generally speaking, a function is considered smooth when its derivatives are small. In the present case, the smoothness of the spectrum being evaluated can be assessed, for example, by measuring how large is the derivative of the spectrum, such as by measuring its maximum, squared error, Euclidian norm, or some alternate norm or distance. Alternatively, one can impose hard limits where the spectrum is sufficiently smooth if the size of the spectrum's derivative falls below some limit, and is rejected if the size is above some limit. This smoothness measure can apply to conventional smoothness (typically, first derivative), to curvature (i.e. second derivative), or to higher-order derivatives.

Being non-negative—

Normalization characteristics—I.e., the spectrum must obey some normalization. For example, when there is no object, one should detect 100% transmission.

Monotonic characteristics—I.e., above (or below) some energy level the spectrum becomes wholly monotonic. This consideration can include both specifically monotonic behavior as well as bi-monotonic behavior.

Envelope limitations—For example, that the spectrum goes (or does not go) to zero at some point.

Quasi-concave characteristics—

Rank—When estimating multiple spectra at once, one could penalize the total rank of the collection of spectra, such as by placing each estimated spectrum in a separate column of a large matrix, then penalizing the rank (or nuclear norm) of that matrix. For example, if we are estimating thousands of spectra (say, one for every view), those spectra might be expected to all fall within some space that, though unknown, is low-dimensional.

Consistency with one or more physics models—There are a number of existing formulae that describe an x-ray spectrum. For example, there is a known formula to describe the so-called Bremsstrahlung type of radiation and the Desbroy-Broyer model is an analytical model for X-ray spectra generation. As yet another example in these regards, the Beer-Lambert law can predict the effects of source filtration and/or detector selectivity. Portions of these models can also be measured or simulated separately. For example, one could generate an analytic model for detector selectivity by first employing an offline Monte Carlo simulation.

Data consistency—In particular, simulated data for the object given a particular spectrum model that accords (or does not accord) with the available imaging data for the object. This can also be referred to as minimizing the data error.

For a physically believable spectrum (or, viewed another way if desired, for a less unbelievable spectrum), one can add a non-negative constraint, minimize the noise-weighted minimum absolute-error (rather than square-error) from the detector measurements, and/or only consider eventually-monotonic answers. Such approaches can be done, for example, using an iterative but efficient linear or quadratic programming solver. More sophisticated constraints can also be added to make the derivatives and support of the spectrum physically believable. Many of these can still be handled by quadratic programming, though some may require more general convex optimization or even non-convex optimization methods. More sophisticated error measures can also be used. In addition to squared error or absolute error, one can also use other options such as a Huber function, or Poisson log-likelihood.

The information regarding the resultant identified spectrum can be employed in a variety of ways. By one optional approach, for example, at optional step 103 the control circuit can select a particular spectrum as a function, at least in part, of the aforementioned evaluation to provide at least one selected spectrum. The control circuit 200, at optional step 104, can then use that selected spectrum(s) when later using other imaging information from this non-invasive imaging apparatus 201 to determine a material constituency of another object (not shown) of uncertain material consistency.

As another example in these regards, the selected spectrum(s) can serve to identify a component of the imaging information that is at least approximately object-nonspecific. This might comprise, for example, identifying a component of the imaging information that is related to an aspect of the non-invasive imaging apparatus 201 other than the primary beam (where the expression "primary beam" will be understood to refer to those x-rays that go straight from the source 202 to detector 204 without deflection (though possibly through an object)). An example in these regards is the so-called sneak path that pertains to x-rays that get to the detector other than through the object (i.e., by sneaking through other paths such as off the ceiling, floor, or walls and/or scatter level).

These teachings can serve, for example to characterize the spectrum for a given x-ray source. These teachings can also serve, however, to characterize the complete x-ray imaging chain (i.e., the x-ray source 202 and the corresponding detector 204) by characterizing the overall effective spectrum (i.e., the spectrum of the source 202 and the energy-dependent response of the detector 204) of the whole system.

It will also be understood that just as a given x-ray source can be capable of more than one energy (and/or a system may have more than one type of detector, and/or the detector may have multiple spectral responses), these teachings can be readily employed to estimate more than one resultant spectrum for a given system. Because these teachings can be done efficiently, it is practical to estimate a different spectrum for every view, using, for example, a beam quality detector. To avoid noise effects, one can smooth or average the detector readings over time before estimating the spectrum and/or smooth the spectral estimates over time.

Additionally, when estimating multiple spectra, one can encourage consistency between spectra. For example, when estimating a separate spectrum for every view, one can encourage all spectra to be somewhat similar, for example by minimizing the rank of the collection of all of those spectra. As another example, when using a single source spectrum and a detector with multiple spectral responses and estimating a separate effective spectrum for each spectral response, we can enforce that there must be a single common source spectrum that is consistent with all of the estimated effective spectra.

As noted above, these teachings can be readily applied with respect to a materials-discrimination application setting where at least one purpose is to identify, at least in part, the material composition of a given object. Using the present teachings one can take a set of conventional radiographic measurements of a set of slabs of known materials and known dimensions. For many application settings these slabs can be considerably smaller than those skilled in the art might expect given past methodologies in these regards. One or more of these slabs could be, for example, a phantom that is manually placed in the beam for a calibration procedure, or a motorized phantom that is automatically placed in the beam for a calibration procedure. These teachings will also accommodate using an auxiliary x-ray detector (i.e., a beam-quality detector as disclosed in U.S. Pat. No. 7,780,352 entitled Radiation System and Radiation Beam Quality Detector and Method, which patent is fully incorporated herein by this reference) consisting of a small number of channels near the x-ray source that receive x-rays but are not in the primary x-ray beam (as might occur, for example, when the X-ray source includes a notch, hole, or other aperture through which escapes a small out-of-plane auxiliary beam), with the slab(s) placed between these channels and the x-ray source. In any of these approaches, it is possible that it may be preferable to use multiple paths as well as multiple materials.

One can then estimate a detailed x-ray spectrum (or pseudo-spectrum) from conventional radiographic measurements captured for this set of slabs. The present teachings will support estimating a physically-believable spectrum, or just estimating a spectrum that is good enough mathematically but not physically believable if desired (i.e., a spectrum that can go negative or have unusual oscillations). These teachings will also accommodate estimating a spectrum in the usual sense (photons as a function of photon energy) or as a pseudo-spectrum that is defined in some transformed space that does not have an obvious physics meaning if desired.

These teachings will also accommodate using a global space to perform the estimation (i.e., with no prior knowledge), or will permit using a restricted space when a priori ideas are available regarding the likely appearance of the spectrum. Such a priori information can derive, for example, from theory or by calibrating the spectrum-space by performing a fuller calibration (using, for example, more slabs) on a few machines.

Accordingly, it will be understood that the detailed spectrum one can obtain by employing these teachings can serve as a calibration point-of-reference for aggressive materials discrimination purposes (or for advanced materials discrimination-like capabilities), or as an intermediate result to generate a materials discrimination calibration table.

By one approach one can use a direct search as is known in the art to find the spectrum (and sneak levels as well, if desired) that minimize the mean-square difference between simulated and measured transmissions (weighted, if desired, by estimated noise) while forcing the solution to be normalized and encouraging the solution to be smooth. In many application settings a satisfactory result can be accomplished without resorting to multiple iterations, by achieving a solution that is (often) physically unbelievable but which may be mathematically sufficient for the application purpose (such as materials discrimination).

Generally speaking, these teachings permit better interpolation and extrapolation between data points as compared to typical prior approaches in these regards. This in turn gives rise to a variety of benefits including more accurate fitting for a given number of data points and smaller maximum object lengths. For example, previously, to get good material discrimination for seven feet (of path length) of organic material, one would typically need to calibrate by scanning at least seven feet of organic material. Using the present teachings, however, one can potentially successfully perform material discrimination on seven feet of organic material by using high quality calibrations that are gained based on only one foot of organic and appropriate short slabs of several other materials (including perhaps some additional even shorter organic slabs).

When applied in a materials-discrimination application setting, these teachings offer more accurate results, the opportunity to calibrate the imaging and processing system using considerably less-expensive phantoms (for example, phantoms costing only a few hundred dollars rather than upwards of fifteen thousand dollars), an ability to facilitate identifying one material that is being shielded by another. For example, when a large smooth object (a "shielding object") lies in front of a small object ("target object"), one can first estimate the material of the shielding object and then use that result to calculate the shielding object's effect on spectrum per the present teachings. One can then calculate the filtered spectrum that is applicable to just the target object. Using such an approach one can effectively remove the shielding object to determine the composition of the target object. Furthermore, by using two or more spectra one may be able to differentiate mixtures that have the same effective atomic number.

The present teachings can also serve to facilitate using simplified calibration procedures and even automated calibration functionality (where, for example, a phantom that is an integrated part of the imaging system's gantry can be readily accommodated). These teachings will also accommodate both master calibration and fine calibration steps (where, for example, the master calibration corresponds to a given machine model number and the fine calibration corresponds to each individual machine).

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. As but one illustrative example in these regards, when estimating the spectrum one may also choose to include some parameters related, for example, to phantom placement or to density, path, or composition. In such a case one can estimate these in conjunction with estimating the spectrum, even though one really only seeks to characterize the spectrum. For example, if one accurately knows the phantom's density, path, and composition, but the orientation of the phantom's assembly relative to the detector is unknown, the present teachings will accommodate adjusting the angle and/or position (within, say, some permit range) to seek a better match.

I claim:

1. An apparatus comprising:

a non-invasive imaging apparatus that utilizes a particular corresponding effective spectrum;

a control circuit operably coupled to the non-invasive imaging apparatus and configured to:

receive imaging information as pertains to an object being imaged by the non-invasive imaging apparatus;

use the imaging information to identify the particular corresponding spectrum by, at least in part, evaluating candidate spectra as a function, at least in part, of physical likelihood.

2. The apparatus of claim 1 wherein the object comprises an object having known physical properties.

3. The apparatus of claim 2 wherein the physical properties include at least one of a path-length dimension, density, and material composition.

4. The apparatus of claim 3 wherein the physical properties include at least both of a projected density and material composition.

5. The apparatus of claim 1 wherein using the imaging information to identify the particular corresponding spectrum for the source of radiation includes, in an appropriate case, identifying a spectrum that is physically unlikely.

6. The apparatus of claim 5 wherein identifying a spectrum that is physically unlikely includes identifying a spectrum that is physically impossible.

7. The apparatus of claim 1 wherein receiving imaging information as pertains to an object being imaged by the non-invasive imaging apparatus comprises receiving imaging information as pertains to a plurality of objects being imaged by the non-invasive imaging apparatus.

8. The apparatus of claim 7 wherein receiving imaging information as pertains to a plurality of objects being imaged by the non-invasive imaging apparatus comprises receiving imaging information as pertains to a plurality of objects being simultaneously imaged by the non-invasive imaging apparatus.

9. The apparatus of claim 1 wherein evaluating the candidate spectra as a function, at least in part, of physical likelihood comprises, at least in part, evaluating the candidate spectra with respect to regularization.

10. The apparatus of claim 1 wherein evaluating the candidate spectra as a function, at least in part, of physical likelihood comprises, at least in part, evaluating the candidate spectra with respect to at least one of:

smoothness;

being non-negative:

normalization characteristics;

monotonic characteristics;

envelope limitations;
quasi-concave characteristics;
consistency with physics models; and
data consistency.

11. The apparatus of claim 1 further comprising:
selecting a particular spectrum as a function, at least in part, of the evaluating of the candidate spectra to thereby provide at least one selected spectrum.

12. The apparatus of claim 11 further comprising:
using the at least one selected spectrum when later using other imaging information from the non-invasive imaging apparatus to determine a material constituency of another object of uncertain material constituency.

13. The apparatus of claim 11 wherein selecting a particular spectrum as a function, at least in part, of the evaluating of the candidate spectra to thereby provide at least one selected spectrum comprises, at least in part, identifying a component of the imaging information that is at least approximately object-nonspecific.

14. A method comprising:
at a control circuit operably coupled to a non-invasive imaging apparatus that utilizes a particular corresponding effective spectrum:
receiving imaging information as pertains to an object being imaged by the non-invasive imaging apparatus;
using the imaging information to identify the particular corresponding spectrum for the source of radiation by, at least in part, evaluating candidate spectra as a function, at least in part, of physical likelihood.

15. The method of claim 14 wherein using the imaging information to identify the particular corresponding spectrum for the source of radiation includes, in an appropriate case, identifying a spectrum that is physically unlikely.

16. The method of claim 15 wherein identifying a spectrum that is physically unlikely includes identifying a spectrum that is physically impossible.

17. The method of claim 14 wherein receiving imaging information as pertains to an object being imaged by the non-invasive imaging method comprises receiving imaging information as pertains to a plurality of objects being simultaneously imaged by the non-invasive imaging method.

18. The method of claim 14 wherein evaluating the candidate spectrum as a function, at least in part, of physical likelihood comprises, at least in part, evaluating the candidate spectra with respect to regularization.

19. The method of claim 14 further comprising:
selecting a particular spectrum as a function, at least in part, of the evaluating of the candidate spectra to thereby provide at least one selected spectrum;
using the at least one selected spectrum when later using other imaging information from the non-invasive imaging apparatus to determine a material constituency of another object of uncertain material constituency.

20. The method of claim 19 wherein selecting a particular spectrum as a function, at least in part, of the evaluating of the candidate spectra to thereby provide at least one selected spectrum comprises, at least in part, identifying a component of the imaging information that is object-nonspecific.

* * * * *